July 8, 1958 F. W. ANDERSON Plant Pat. 1,725

PEACH TREE

Filed Oct. 29, 1957

WITNESS

Addison J. Avery

INVENTOR

Frederic W. Anderson

Webster & Webster

ATTYS.

United States Patent Office

Plant Pat. 1,725
Patented July 8, 1958

1,725

PEACH TREE

Frederic W. Anderson, Merced, Calif., assignor to Kim Bros., Reedley, Calif.

Application October 29, 1957, Serial No. 693,223

1 Claim. (Cl. 47—62)

The present invention embraces a new and distinct variety of peach tree which bears white fleshed, clingstone fruit having a bright red surface color which substantially overspreads a pale greenish-yellow ground color; the fruit being especially characterized by a very early ripening period.

This variety was originated by me at my fruit breeding orchard located near Merced, California, during the conduct of an extended program in the development of commercially desirable peaches.

More particularly, the instant variety of peach tree resulted from a cross of the Sun Grand nectarine (United States Plant Patent No. 980) × the Robin peach (United States Plant Patent No. 529). Seeds from such cross were planted, and all of the resulting seedlings were white fleshed peaches which—in maturity—had widely varying ripening periods; one of such seedlings, and which is the variety herein described and claimed, having evidenced the earliest maturity, being approximately one week before the Mayflower peach (unpatented), and at the same time as the Springtime peach (United States Plant Patent No. 1,268).

By reason of such early ripening period—and other desirable qualities, as will hereinafter appear—the variety was selected by me for reproduction, and was therefore subsequently top-worked on orchard trees in my fruit breeding orchard, located as aforesaid.

Such asexual reproductions by top-working were found—when they came into bearing—to carry forward all of the characteristics of the original seedling.

As compared with the Springtime peach, the two varieties are somewhat similar in that in addition to a like ripening period, the fruit of both is generally small, white fleshed, and clingstone. They are distinct, however, as the fruit of the present variety has large showy flowers, and leaves with reniform glands, while the Springtime peach has small non-showy flowers, and leaves with globose glands; the fruit here being slightly larger, firmer, brighter red in surface color, not quite so protuberant at the apex, and less subject to defects.

Figure 1:
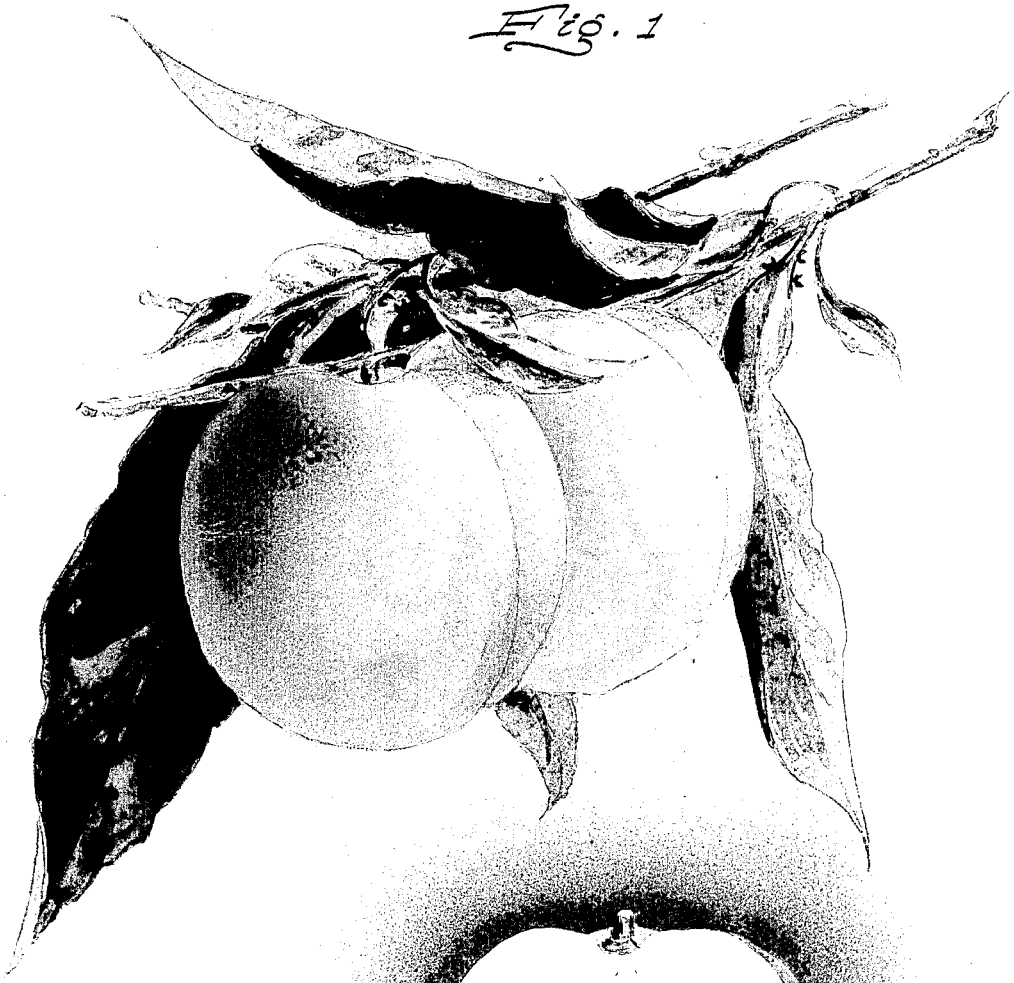
Fig. 1 is an elevation showing two of the fruit, together with twigs and leaves.
Figure 2:
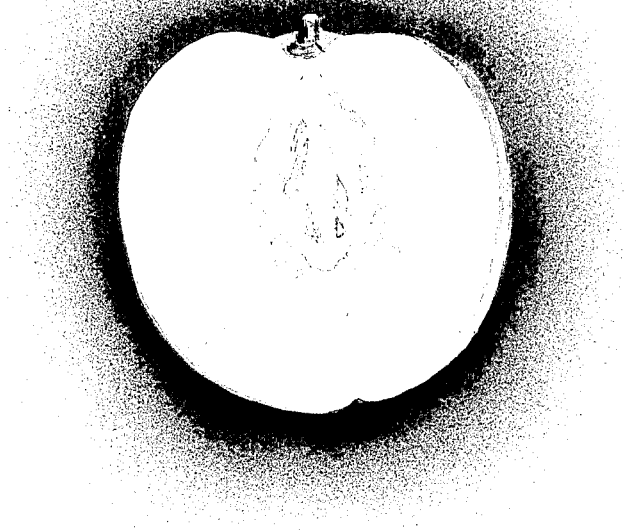
Fig. 2 is a sectional elevation of one of the fruit, with the stone exposed; such stone only partially showing through retained flesh.

Referring now more specifically to the pomological details of this new and distinct variety of peach tree, the following is an outline description thereof; all major color plate identifications being by reference to Maerz and Paul Dictionary of Color:

Tree:
- *Size.*—Medium.
- *Vigor.*—Vigorous.
- *Growth.*—Spreading.

- *Density.*—Open.
- *Production.*—Productive.
- *Bearing.*—Regular bearer.

Trunk: Size—medium.

Branches: Size—medium.

Leaves:
- *Size.*—Medium Average length—5½" to 6". Average width—1¼" to 1½".
- *Form.*—Lanceolate.
- *Thickness.*—Medium.
- *Texture.*—Smooth.
- *Margin.*—Crenate.
- *Petiole.*—Medium length; medium thickness.
- *Glands.*—Average number—three. Reniform; usually positioned two on petiole and one to three on blade.
- *Stipules.*—Narrow, and drop early.
- *Color.*—Top side—medium green (22–L–8), with slight yellow cast. Under side—lighter green (22–K–6).

Flower buds:
- *Size.*—Medium.
- *Pubescence.*—Pubescent.

Flowers:
- *Blooming period.*—Early as compared with other varieties.
- *Date of first bloom.*—March 1, 1957.
- *Date of full bloom.*—March 15, 1957.
- *Size.*—Large—showy.

Fruit:
- *Maturity when described.*—Eating ripe, May 25, 1957.
- *Date of first picking.*—May 24, 1957.
- *Date of last picking.*—May 31, 1957.
- *Size.*—Uniform; medium to small. Average diameter axially—2⅜". Average transversely in suture plane—2¼".
- *Form.*—Uniform; symmetrical; globose.
- *Suture.*—An inconspicuous line extending from base to apex, with slight depression beyond pistil point.
- *Ventral surface.*—Rounded; lips equal.
- *Cavity.*—Rounded. Average depth—¼". Average breadth—½".
- *Base.*—Rounded.
- *Apex.*—Prolonged; rounded.
- *Pistil point.*—Apical.

Skin:
- *Thickness.*—Medium.
- *Texture.*—Medium.
- *Tenacity to flesh.*—Free.
- *Tendency to crack.*—None.
- *Down.*—Moderate; short.
- *Color.*—Pale greenish yellow ground color (10–L–1, shading to 11–B–6), substantially overspread with a relatively bright red—(5–K–10, shading to 7–L–7).

Flesh:
- *Amygdalin.*—Wanting.
- *Juice.*—Abundant; watery.
- *Texture.*—Soft; melting.
- *Fibers.*—Few; tender.
- *Ripens.*—Earliest at apex.
- *Flavor.*—Acid to sub-acid.
- *Aroma.*—Pronounced.
- *Eating quality.*—Fair to good.
- *Color.*—Whitish (9–B–1, shading to 10–B–2).

Stone:
- *Type.*—Cling; adheres to flesh over entire surface.

*Size.*—Medium to small. Average length—1¼". Average breadth—¾". Average thickness—⅝".
*Form.*—Ovoid.
*Base.*—Straight.
*Hilum.*—Oval.
*Apex.*—Acute.
*Sides.*—Equal.
*Surface.*—Irregularly furrowed toward apex—pitted toward base.
*Ridges.*—Rounded toward apex; interrupted.
*Pits.*—Elongated.
*Ventral edge.*—Thick, with wing toward base.
*Dorsal edge.*—Narrow, with shallow groove.
*Tendency to split.*—Slight.
*Color.*—Golden wheat (11–D–7).

Use: Local; dessert.
Keeping quality: Medium to poor.
Shipping quality: Medium to poor.

The tree and its fruit herein described may vary in slight detail due to climatic and soil conditions under which the variety may be grown.

The following is claimed:

A new and distinct variety of peach tree, as illustrated and described, which bears white fleshed, clingstone fruit having a red surface color substantially overspreading a pale greenish-yellow ground color, and particularly characterized by an early ripening period approximately one week before the Mayflower peach, and with the Springtime peach; and further characterized—in comparison with said Springtime peach—by large showy flowers, leaves with reniform glands, and fruit which is larger, firmer, brighter red in surface color, not quite so protuberant at the apex, and less subject to defects.

No references cited.